US012350080B2

(12) United States Patent
Gleich

(10) Patent No.: US 12,350,080 B2
(45) Date of Patent: Jul. 8, 2025

(54) X-RAY MODULATOR

(71) Applicant: KONINKLIJKE PHILIPS N.V., Eindhoven (NL)

(72) Inventor: Bernhard Gleich, Hamburg (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 253 days.

(21) Appl. No.: 18/033,873

(22) PCT Filed: Oct. 27, 2021

(86) PCT No.: PCT/EP2021/079744
§ 371 (c)(1),
(2) Date: Apr. 26, 2023

(87) PCT Pub. No.: WO2022/096328
PCT Pub. Date: May 12, 2022

(65) Prior Publication Data
US 2023/0397895 A1  Dec. 14, 2023

(30) Foreign Application Priority Data
Nov. 3, 2020 (EP) .................... 20205342

(51) Int. Cl.
*A61B 6/40* (2024.01)
*A61B 6/00* (2006.01)
*A61B 6/03* (2006.01)

(52) U.S. Cl.
CPC .............. *A61B 6/405* (2013.01); *A61B 6/032* (2013.01); *A61B 6/482* (2013.01)

(58) Field of Classification Search
CPC ......... A61B 6/405; A61B 6/032; A61B 6/482; A61B 6/4035; G21K 1/10
See application file for complete search history.

(56) References Cited

U.S. PATENT DOCUMENTS

| | | | | |
|---|---|---|---|---|
| 5,195,121 | A | * | 3/1993 | Charrier .................... G21K 1/02 378/160 |
| 5,353,323 | A | * | 10/1994 | Hirokawa ........... G03F 7/70866 378/34 |
| 7,968,853 | B2 | | 6/2011 | Altman |
| 2013/0287164 | A1 | | 10/2013 | Rogers |
| 2014/0328453 | A1 | | 11/2014 | Hsieh |
| 2019/0269375 | A1 | | 9/2019 | Harrison |

FOREIGN PATENT DOCUMENTS

DE  19638621 C1  2/1998

OTHER PUBLICATIONS

PCT International Search Report, International application No. PCT/EP2021/079744, Jan. 7, 2022.

* cited by examiner

*Primary Examiner* — Courtney D Thomas
(74) *Attorney, Agent, or Firm* — Larry Liberchuk

(57) ABSTRACT

The invention provides an X-ray modulator, for use with an X-ray tube, comprising an enclosed chamber having a window portion and a side portion in gaseous communication with each other. The enclosed chamber comprises a chamber wall, wherein the chamber wall of the window portion is thinner than the chamber wall of the side portion. The X-ray modulator further comprises a pressure modulation device provided in the side portion of the enclosed chamber, which is adapted to modulate the pressure within the enclosed chamber, and an absorption gas within the enclosed chamber for absorbing X-ray radiation.

15 Claims, 4 Drawing Sheets

X-RAY MODULATOR

FIELD OF THE INVENTION

The invention relates to the field of X-ray imaging, and more specifically to the field of spectral computed tomography imaging.

BACKGROUND OF THE INVENTION

Spectral imaging is becoming an increasingly popular imaging methodology of X-ray computed tomography. Spectral imaging is performed by applying different energy settings, such as different voltages, to an X-ray tube, which results in different X-ray spectra being provided to a subject. In this way, quantitative image data may be obtained that allows a decomposition of a scanned object, such as a subject's body, into different materials and tissues.

One of the methods for performing spectral imaging is kVp switching, wherein two different voltages are alternately applied across an X-ray tube. The fast change of X-ray tube supply voltage, by fast kVp switching, is an efficient and inexpensive way to accomplish spectral imaging. The overall measurements can be split into two different sinograms, one consisting of those measurements taken with the high energy spectrum and the other one taken with the low energy spectrum.

The image quality of a spectral CT image may be impaired by non-optimal spectral separation of the photons generated at the different energy levels, also referred to as electrical tensions. In particular, at higher energies, a high proportion of low energy photons may be generated, thereby shifting the average photon energy of the high energy image closer to that of the low energy image and reducing the spectral separation.

There is therefore a need for a means of reducing the number of low energy photons incident on the subject during the high energy imaging stage of a spectral imaging method.

SUMMARY OF THE INVENTION

The invention is defined by the claims.

According to examples in accordance with an aspect of the invention, there is provided an X-ray modulator, for use with an X-ray tube, the X-ray modulator comprising:
  an enclosed chamber having a window portion and a side portion, wherein the window portion is in gaseous communication with the side portion, the enclosed chamber comprising a chamber wall, wherein the chamber wall of the window portion is thinner than the chamber wall of the side portion;
  a pressure modulation device provided in the side portion of the enclosed chamber and adapted to modulate the pressure within the enclosed chamber; and
  an absorption gas within the enclosed chamber for absorbing X-ray radiation. The X-ray modulator provides a means of absorbing unwanted low-energy photons during spectral CT imaging, thereby improving the spectral separation of the photons and so improving the image quality of the obtained spectral CT image.

By providing an absorber in the form of a gas, the required high insertion speeds for the absorber may be achieved without adversely affecting the image quality by the shadow of an alternative absorber moving across the field of view.

In an embodiment, the absorption gas comprises one or more of:
  xenon; and
  iodine vapor.

In an embodiment, the X-ray modulator comprises a heating element.

In this way, the pressure within the enclosed chamber may be regulated with greater accuracy.

In an embodiment, the absorption gas is iodine vapor, and wherein the X-ray modulator comprises a layer of protective material within the enclosed chamber disposed on the chamber wall, and optionally wherein the protective material is silver.

In this way, the enclosed chamber is protected from the corrosive effects of iodine.

In an embodiment, the chamber walls on opposing sides of the enclosed chamber are separated by a given separation distance, wherein the average separation distance at the window portion is less than the average separation distance at the side portion, the side portion having a tapered structure with a minimum separation distance adjacent the window portion, the minimum separation distance being greater than or equal to the average separation distance at the window portion, and a maximum separation distance distal to the window portion and optionally wherein the pressure modulator is positioned in a region of maximum separation distance within the side portion.

In this way, the increase in pressure within the window portion may be amplified, thereby reducing the required increase in pressure within the side portion. Thus, the pressure generated by the pressure modulator within the side portion may be maximally amplified within the window portion.

In an embodiment, the pressure modulator comprises one or more of:
  a speaker;
  a transducer element; and
  an electroactive polymer.

In an embodiment, the pressure modulator is adapted to modulate the pressure within an average pressure range of 1 MPa to 35 Mpa, the average pressure being the average pressure within the enclosed chamber.

In an embodiment, the chamber wall comprises:
  a first material at the side portion, the first material comprising one or more of:
    aluminum;
    titanium; and
    steel;
  a second material at the window portion, the second material comprising one or more of:
    beryllium;
    boron carbide;
    boron nitride
    magnesium;
    diamond; and
    aluminum.

In an embodiment, the X-ray modulator further comprises a pump adapted to generate a flow of absorption gas between the side portion and the window portion.

In this way, the temperature of the absorption gas may be regulated, thereby preventing the gas from overheating under continued X-ray irradiation.

In an embodiment, the X-ray modulator comprises a mechanical resonator structure.

In this way, the pressure within the enclosed chamber may be increased further without requiring additional actively driven hardware.

In an embodiment, the X-ray modulator comprises a plurality of side portions, each side portion having a pressure modulator.

In an embodiment, the X-ray modulator has an elliptical cross section, the cross section of the side portion being an elliptical annulus and the cross section of the window portion being an ellipse within the elliptical annulus of the side portion.

In an embodiment, the X-ray modulator is disposed within a vacuum chamber.

In this way, the amplitude of the sound generated by the X-ray modulator, as heard by a user, may be reduced.

According to examples in accordance with an aspect of the invention, there is provided a computed tomography, CT, imaging system comprising:
- an X-ray tube adapted to generate X-ray radiation, the X-ray tube having an emission window for the X-ray radiation to pass through;
- an X-ray modulator as described above, wherein the window portion of the X-ray modulator is positioned adjacent the emission window of the X-ray tube such that the X-ray radiation generated by the X-ray tube passes through the window portion of the X-ray modulator;
- a detector adapted to detect X-ray radiation; and
- a processing unit adapted to control the CT imaging system.

In an embodiment, the system is adapted to operate the X-ray tube at a first electrical tension and a second electrical tension, the first electrical tension being higher than the second electrical tension, and wherein the pressure modulator is adapted to modulate the pressure within the enclosed chamber between a first pressure and a second pressure, wherein the first pressure is higher than the second pressure, and wherein the X-ray tube and the pressure modulator are operated such that the first pressure occurs at the same time as the first electrical tension and the second pressure occurs at the same time as the second electrical tension.

In this way, the optical attenuation characteristics of the absorption gas, which are determined by the pressure of the absorption gas, may be controlled to increase the number of low energy photons absorbed during the high electrical tension phase, when unwanted low energy photons are abundant, and decrease photonic absorption during the low electrical tension phase, when photonic absorption is not desirable.

These and other aspects of the invention will be apparent from and elucidated with reference to the embodiment(s) described hereinafter.

BRIEF DESCRIPTION OF THE DRAWINGS

For a better understanding of the invention, and to show more clearly how it may be carried into effect, reference will now be made, by way of example only, to the accompanying drawings, in which.

DETAILED DESCRIPTION OF THE EMBODIMENTS

Figure 1:
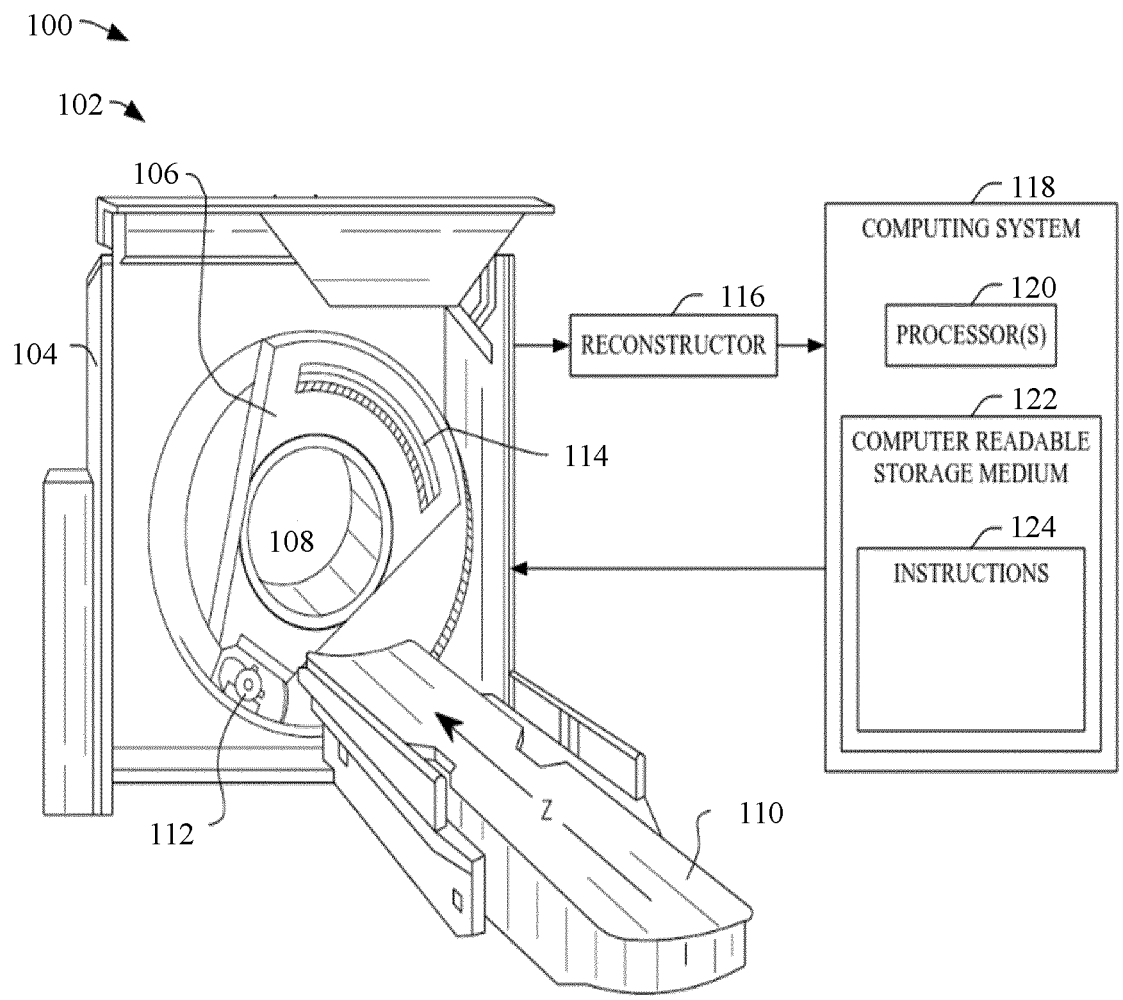
FIG. 1 schematically illustrates a CT imaging system.

The invention will be described with reference to the Figures.

It should be understood that the detailed description and specific examples, while indicating exemplary embodiments of the apparatus, systems and methods, are intended for purposes of illustration only and are not intended to limit the scope of the invention. These and other features, aspects, and advantages of the apparatus, systems and methods of the present invention will become better understood from the following description, appended claims, and accompanying drawings. It should be understood that the Figures are merely schematic and are not drawn to scale. It should also be understood that the same reference numerals are used throughout the Figures to indicate the same or similar parts.

The invention provides an X-ray modulator, for use with an X-ray tube, comprising an enclosed chamber having a window portion and a side portion in gaseous communication with each other. The enclosed chamber comprises a chamber wall, wherein the chamber wall of the window portion is thinner than the chamber wall of the side portion.

The X-ray modulator further comprises a pressure modulation device provided in the side portion of the enclosed chamber, which is adapted to modulate the pressure within the enclosed chamber, and an absorption gas within the enclosed chamber for absorbing X-ray radiation.

A conventional computed tomography (CT) scanner includes an X-ray radiation generator mounted on a rotatable gantry opposite one or more integrating detectors. The X-ray generator rotates around an examination region located between the X-ray generator and the one or more detectors and emits (typically polychromatic) radiation that traverses the examination region and a subject and/or object disposed in the examination region. The one or more detectors detect radiation that traverses the examination region and generate a signal (or projection data) indicative of the examination region and the subject and/or object disposed therein. The projection data refers to the raw detector data, and can be used to form a projection sinogram, the latter being a visual representation of the projection data captured by the detector(s).

A reconstructor is typically further used to process the projection data and reconstruct a volumetric image of the subject or object. The volumetric image is composed of a plurality of cross-sectional image slices which are each generated from the projection data through a process of tomographic reconstruction, such as through application of a filtered back projection algorithm. The reconstructed image data is effectively an inverse radon transform of the raw projection data.

FIG. 1 schematically illustrates a system 100 including an imaging system 102 such as a CT scanner configured for spectral (multi-energy) imaging. The imaging system 102 includes a generally stationary gantry 104 and a rotating gantry 106, which is rotatably supported by the stationary gantry 104 and rotates around an examination region 108 about a z-axis. A subject support 110, such as a couch, supports an object or subject in the examination region 108.

A radiation source 112, such as an X-ray tube, is rotatably supported by the rotating gantry 106, rotates with the rotating gantry 106, and emits radiation that traverses the examination region 108. In one instance, the radiation source 112 includes a single broad spectrum X-ray tube. In another instance, the radiation source 112 includes a single X-ray tube configured to switch between at least two different emission voltages (e.g., 80 kVp and 140 kVp) during scanning. In yet another instance, the radiation source 112 includes two or more X-ray tubes configured to emit radiation having different mean spectra. In still another instance, the radiation source 112 includes a combination thereof.

A radiation sensitive detector array 114 subtends an angular arc opposite the radiation source 112 across the examination region 108. The radiation sensitive detector array 114 detects radiation traversing the examination region 108 and generates an electrical signal(s) (projection data) indicative thereof. Where the radiation source 112 includes a single broad spectrum X-ray tube, the radiation sensitive detector array 112 includes energy-resolving detectors (e.g., direct conversion photon counting detectors, at least two sets of scintillators with different spectral sensitivities (multi-layer), etc.). With kVp switching and multi-tube configurations, the detector array 114 can include single layer detectors, direct conversion photon counting detectors, and/or multi-layer detectors. The direct conversion photon counting detectors may include a conversion material such as CdTe, CdZnTe, Si, Ge, GaAs, or other direct conversion material. An example of multi-layer detector includes a double decker detector such as the double decker detector described in U.S. Pat. No. 7,968,853 B2, filed Apr. 10, 2006, and entitled "Double Decker Detector for Spectral CT".

A reconstructor 116 receives spectral projection data from the detector array 114 and reconstructs spectral volumetric image data such as sCCTA image data, a high-energy image, a low energy image, a photoelectric image, a Compton scatter image, an iodine image, a calcium image, a virtual non-contrast image, a bone image, a soft tissue image, and/or other basis material image. The reconstructor 116 can also reconstruct non-spectral volumetric image data, e.g., by combining spectral projection data and/or spectral volumetric image data. Generally, the spectral projection data and/or spectral volumetric image data will include data for at least two different energies and/or energy ranges.

A computing system 118 serves as an operator console. The console 118 includes a human readable output device such as a monitor and an input device such as a keyboard, mouse, etc. Software resident on the console 118 allows the operator to interact with and/or operate the scanner 102 via a graphical user interface (GUI) or otherwise. The console 118 further includes a processor 120 (e.g., a microprocessor, a controller, a central processing unit, etc.) and a computer readable storage medium 122, which excludes non-transitory medium, and includes transitory medium such as a physical memory device, etc. The computer readable storage medium 122 includes instructions 124 for the operation of the imaging system. The processor 120 is configured to execute the instructions 124. The processor 120 may additionally be configured to execute one or more computer readable instructions carried by a carrier wave, a signal and/or other transitory medium. In a variation, the processor 120 and the computer readable storage medium 122 are part of another computing system, which is separate from the computing system 118.

As discussed above, a common problem with spectral imaging is the non-optimal spectral separation of the photons generated at the different energies. The inventors have recognized that, in principle, the low energy photons generated during the high energy imaging stage may be eliminated using an absorber material with an atomic number of around 50. Enough photons are generated at the high imaging energy that the use of such an absorber would not increase scan time or available dose in a significant manner. However, the required insertion speed of the absorption material in front of the emission window of an X-ray tube of over 100 m/s makes the incorporation of such an absorption in an X-ray tube difficult.

Figure 2:
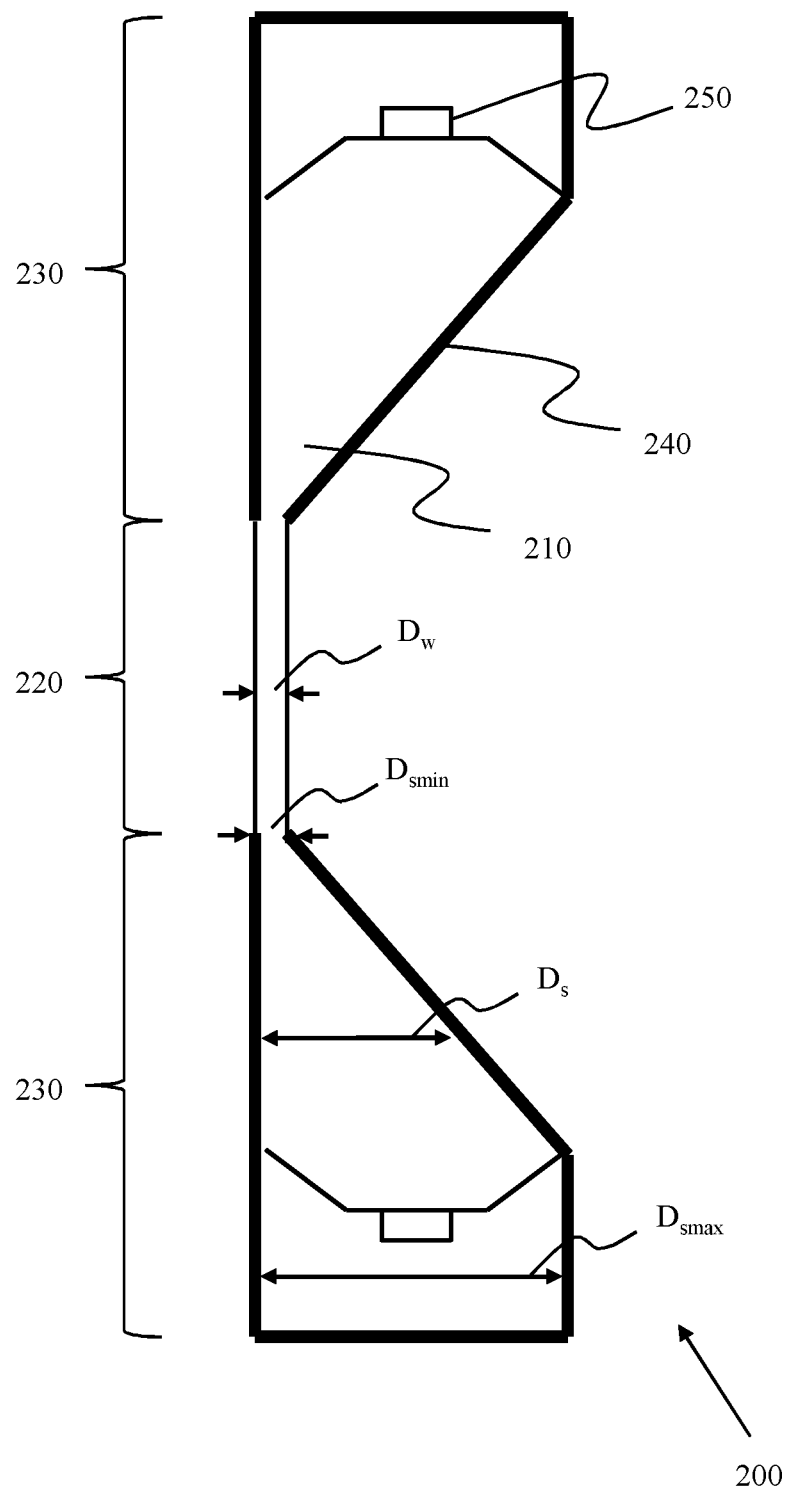
FIG. 2 shows an example of an X-ray modulator according to an aspect of the invention.

FIG. 2 shows an example of an X-ray modulator 200 for use with an X-ray tube.

The X-ray modulator 200 comprises an enclosed chamber 210 having a window portion 220 and a side portion 230. In the example shown in FIG. 1, the X-ray modulator comprises two identical side portions positioned either side of the window portion. Any number of one or more side portions may be positioned about the window portion in order to form the X-ray modulator according to the invention.

The window portion is in gaseous communication with the side portion. In other words, the side portion(s) and the window portion form one continuous enclosed chamber.

The enclosed chamber 210 is defined by a chamber wall 240, wherein the chamber wall of the window portion is thinner than the chamber wall of the side portion. The chamber wall may be made from two different materials, the first material being used in the chamber wall of the side portion and the second material being used in the chamber wall of the window portion.

The first material, in the chamber wall 240 at the side portion 230, may be a rigid material, such as: aluminum; titanium; steel; and the like. The first material does not need to be permeable to X-ray radiation and so may be as thick as reasonably possible, which ensures that the movement of the X-ray modulator 200 is minimized when the internal pressure of the X-ray modulator changes during use.

The second material, in the chamber wall 240 at the window portion 220, needs to become thinner than the first material in order to be sufficiently transparent to X-rays. In addition, the reduced thickness means that the second material may be a stiffer material than the first material in order to maintain the integrity of the X-ray modulator under changes in pressure within the enclosed chamber 210. The second material may be: beryllium; boron carbide; boron nitride; magnesium; diamond; or aluminum. Further, the window portion may be curved and/or provided with reinforcement ribs to further improve the rigidity of the window portion.

The X-ray modulator 200 further comprises a pressure modulation device 250 provided in the side portion 230 of the enclosed chamber 210 and adapted to modulate the pressure within the enclosed chamber. The pressure modulator may be: a speaker; a transducer element, such as a piezoelectric device or a magnetostricitve device; an electroactive polymer; or any suitable device for modulating the pressure within the enclosed chamber. The pressure modulation device should be resistive to the absorption gas, or gases, within the enclosed chamber.

The X-ray modulator 200 further comprises an absorption gas within the enclosed chamber 210 for absorbing X-ray radiation, and in particular absorbing the low energy photons generated during the high energy imaging period.

The problem with the fast insertion of the absorber is solved by using a gas as an absorber as gas flow speeds can be in the order of the speed of sound. Moreover, due to gradual pressure increase, there are no adverse effects on the image quality by the shadow of the absorber moving across the field of view.

As described above, in order to perform spectral CT imaging, at least two electrical tensions are generated at the X-ray tube. At the lower electrical tension, as the efficiency of the X-ray tube is low at the lower tension, it is desirable to absorb as few photons as possible; however, at the higher electrical tension, there is an abundance of unwanted low energy photons, which need to be absorbed. Accordingly, the optical attenuation of the absorption gas needs to be controlled based on the electrical tension of the X-ray tube. As discussed below, the optical attenuation of the absorption gas is determined by the density of the absorption gas, which is determined by the pressure and temperature of the gas.

Accordingly, at the lower electrical tension, the pressure modulation device may be operated to bring the pressure within the enclosed chamber as low as possible and, at the higher electrical tension, the pressure modulation device may be operated to bring the pressure to the desired level to absorb the low energy photons.

Gas pressure cannot be changed with infinite speed, meaning that the change in pressure within the enclosed chamber will be sinusoidal in nature. Accordingly, the pressure changes may be aligned with the voltage changes within the X-ray tube, with low pressure occurring during the lower electrical tension and high pressure occurring during the higher electrical tension.

In practice, the time ratio between the lower electrical tension and the higher electrical tension is not 1 to 1 for optimum spectral separation, while having enough X-ray flux from the X-ray tube to complete the image formation in the desired time. However, the pressure changes are most simply achieved when the time ratio is close to 1 to 1. By changing the average pressure within the X-ray modulator, and the pressure amplitude, the optimal conditions for the entire imaging system can be brought closer to the 1 to 1 time ratio operation. In this case, a simple single frequency resonance may be utilized for the whole system, which is beneficial as the utilization of resonance reduces the drive power requirements for the pressure modulation device.

Put another way, during spectral imaging, the CT imaging system may be adapted to operate the X-ray tube at a first electrical tension and a second electrical tension, wherein the first electrical tension is higher than the second electrical tension.

Further, the pressure modulator may be adapted to modulate the pressure within the enclosed chamber between a first pressure and a second pressure, wherein the first pressure is higher than the second pressure.

The system may operate the X-ray tube and the pressure modulator such that the first pressure occurs at the same time as the first electrical tension and the second pressure occurs at the same time as the second electrical tension.

If a 1 to 1 time ratio between the two electrical tensions cannot be reached, the X-ray modulator may be designed to operate at a multi-frequency resonance. The desired pressure wave may be decomposed into a Fourier series, from which the first two to ten components of the series may be generated by pressure modulation devices. The X-ray modulator may have resonances at, or close to, the harmonics of the Fourier series.

The optical attenuation of the absorption gas is determined by the density of the absorption gas, which is determined by the pressure and temperature of the absorption gas. This is demonstrated theoretically below; however, it should be noted that the following passages ignore the partial adiabatic nature of the compression of the absorption gas due to the changes in pressure. In practice, the operation frequency of the X-ray modulator is between 1 kHz and 5 kHz and the heat exchange to the environment surrounding the X-ray modulator is small. Accordingly, the behavior of the absorption gas may be approximated as isothermal; however, in reality the gas will exhibit behavior between adiabatic and isothermal behaviors. For the purposes of providing a simplified explanation of how the absorption gas behaves in the enclosed chamber, isothermal behavior will be assumed in the following explanation.

The ideal gas equation, which is appropriate in this example as the absorption gas is held in an enclosed chamber, is given as:

$$PV=nRT \quad (1)$$

wherein: P is the pressure within the enclosed chamber; V is the volume of the enclosed chamber; n is the number of mole of absorption gas present in the enclosed chamber; R is the ideal gas constant; and T is the temperature of the absorption gas.

The optical attenuation of a substance is described by the Beer-Lambert law, which, for a physical material containing a single attenuating species of uniform concentration along an optical path, may be written as:

$$A=\varepsilon cl \quad (2)$$

wherein: A is the optical attenuation number; c is the molar attenuation coefficient of the absorption gas; c is the concentration of the absorption gas within the enclosed chamber; and l is the optical path length through the absorption gas.

The concentration, c, of the absorption gas is given by:

$$c = \frac{n}{V} \quad (3)$$

Substituting for c in equation (2) using equation (3) and rearranging, the following relation is obtained:

$$V = \frac{\varepsilon nl}{A} \quad (4)$$

Substituting for V in equation (1) using equation (4) and rearranging, the following relation is obtained:

$$A = \left(\frac{\varepsilon l}{RT}\right)P \quad (5)$$

Accordingly, the amount of optical attenuation caused by the absorption gas is determined by the pressure of the absorption gas. As noted above, the equations provided above describe the behavior of the absorption gas in an isothermal approximation. In practice, changes in temperature and heat transfer will need to be accounted for in order to accurately control the behavior of the absorption gas.

A suitable gas for the absorption gas is xenon, or a mixture of xenon with another gases such as nitrogen, which achieves the desired optical attenuation with an optical path length of only one to a few millimeters at, for example, a pressure of 10 MPa. The average pressure within the enclosed chamber may be in the region of 10 MPa, and within a range of 1 MPa to 35 MPa, the peak pressure may reach 35 MPa and the minimum pressure may be roughly 1 MPa. The pressure ratio between the peak pressure point and the minimum pressure point in the window portion should may be at least 1.5, and may be more than 3. In order to achieve the desired pressure, the pressure modulator device, which may be an electrodynamic speaker, may be operated at a frequency in the region of 3 kHz. The pressure modulator device may operate at a frequency that matches a harmonic of the kVp switching frequencies. The X-ray modulator may be enclosed within an additional vacuum chamber to provide sound insulation.

An alternative absorption gas material may be iodine vapor, in which case, in order to prevent damage to the X-ray modulator due to exposure to corrosive iodine, the X-ray modulator may comprise a layer of protective material, such as silver, within the enclosed chamber disposed on the chamber wall. Further, if iodine is used, a heating mechanism may be incorporated into the X-ray modulator in order to maintain the desired average pressure within the enclosed chamber. The iodine vapor may be used in conjunction with a further gas, such as nitrogen, xenon and the like.

As described above, the pressure modulator device may include a speaker; however, a conventional speaker may not be capable of increasing the pressure within the enclosed chamber up to 10 MPa. In order to achieve the desired pressure within the enclosed chamber, the X-ray modulator may have a resonance at the desired operation frequency of the frequency modulation device, for example, up to 5 kHz. The operation frequency if the frequency modulation device may also align with the frequency with the CT gantry rotations. Further, the X-ray modulator may have multiple resonances to accommodate different CT gantry rotations.

In addition, the X-ray modulator 200 may have a horn structure, which amplifies the pressure wave generated by the pressure modulation device 250 towards the window portion 220.

Put another way, the chamber walls on opposing sides of the enclosed chamber 210 are separated by a given separation distance, wherein the average separation distance at the window portion, $D_w$, 220 is less than the average separation distance at the side portion, $D_s$, 230. The side portion has a tapered structure, or horn structure, with a minimum separation distance, $D_{smin}$, adjacent the window portion, the minimum separation distance being greater than or equal to the average separation distance at the window portion, and a maximum separation distance, $D_{smax}$, distal to the window portion. As the pressure modulator device 250 is positioned in a region of maximum separation distance within the side portion, a pressure wave generated in the region of maximum separation distance will be constricted as the separation distance between the chamber walls decreases. Accordingly, an increase in pressure in the side portion will result in a proportionally larger increase in pressure in the window portion.

In addition, the X-ray modulator may include a mechanical resonator structure. A mechanical resonator structure may be adapted to tune the resonance of the X-ray modulator to a desired frequency. Alternatively, or in addition to the mechanical resonator structure, resonance tuning may be performed by altering the temperature of the enclosed chamber, for example by way of a heating element, particularly if the change in temperature introduces a light gas like water vapor by evaporation.

During use, the average pressure within the enclosed chamber is brought to a suitable value to achieve the desired optical attenuation. For example, if the window portion has a separation distance, $D_w$, of 1 mm wide, a pressure of around 10 MPa may be suitable. However, the pressure may be decreased if a larger separation distance in the window portion 220 is provided, as this provides a larger optical path length for the radiation to pass through, the optical path length being dependent on the optical attenuation as shown above in equation (5).

Figure 3:
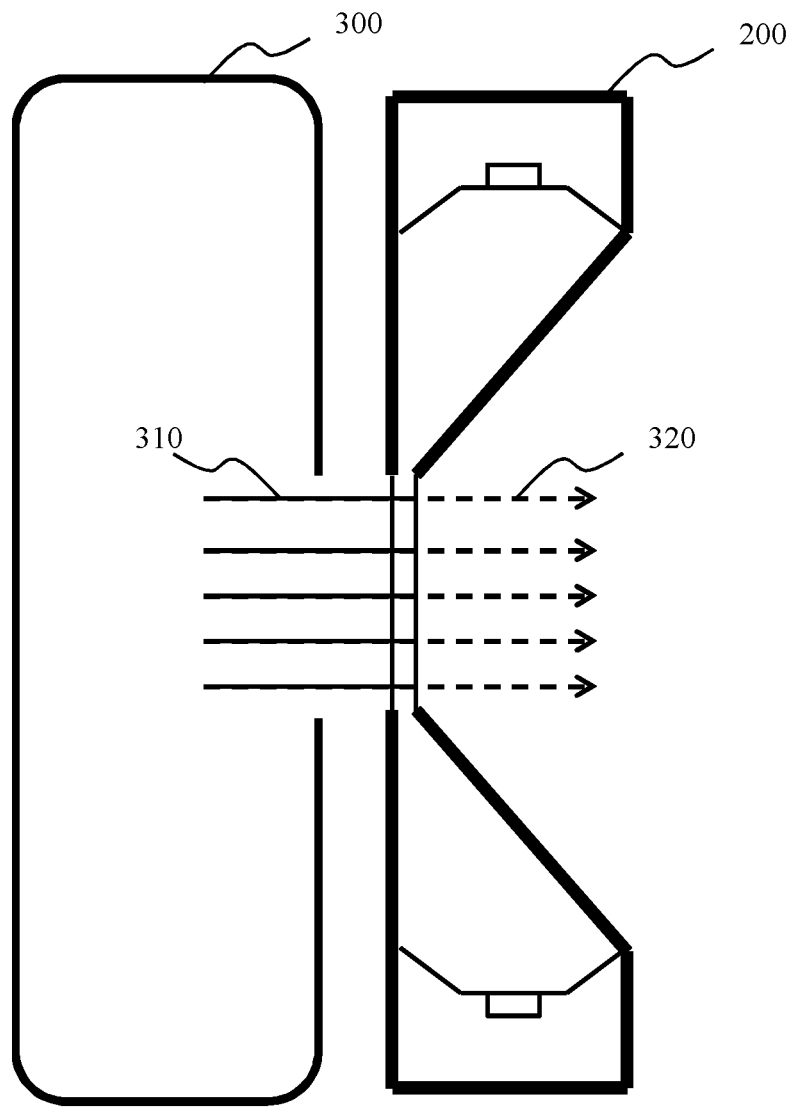
FIG. 3 shows the X-ray modulator of FIG. 2 together with an X-ray tube.

FIG. 3 shows the X-ray modulator 200, as shown in FIG. 2, together with an X-ray tube 300.

X-ray radiation 310 generated in the X-ray tube 300 passes through the window portion of the X-ray modulator 200. As discussed above, when X-rays are generated at the higher energy level during a spectral imaging procedure, unwanted low energy photons are also generated and leave the X-ray tube. As the radiation from the X-ray tube passes through the window portion of the X-ray modulator 200, the low energy photons are absorbed by the absorption gas within the enclosed chamber of the X-ray modulator, thereby generating modulated X-rays 320 comprising only, or predominantly, high energy photons. In this way, the spectral separation between the low energy and high energy levels is increased, thereby improving the image quality of the spectral images.

The window portion of the X-ray modulator 200 may be subjected to a high thermal flux from the X-ray tube 300, and in particular the X-ray anode within the tube. Thus, the X-ray modulator may include a means of facilitating cooling the absorption gas. For example, to facilitate cooling, the absorption gas may be subjected to a steady flow through the window portion of the X-ray modulator, for example, by way of a pump transporting the absorption gas between the side portions of the X-ray modulator causing a flow of absorption gas through the window portion.

Figure 4A:
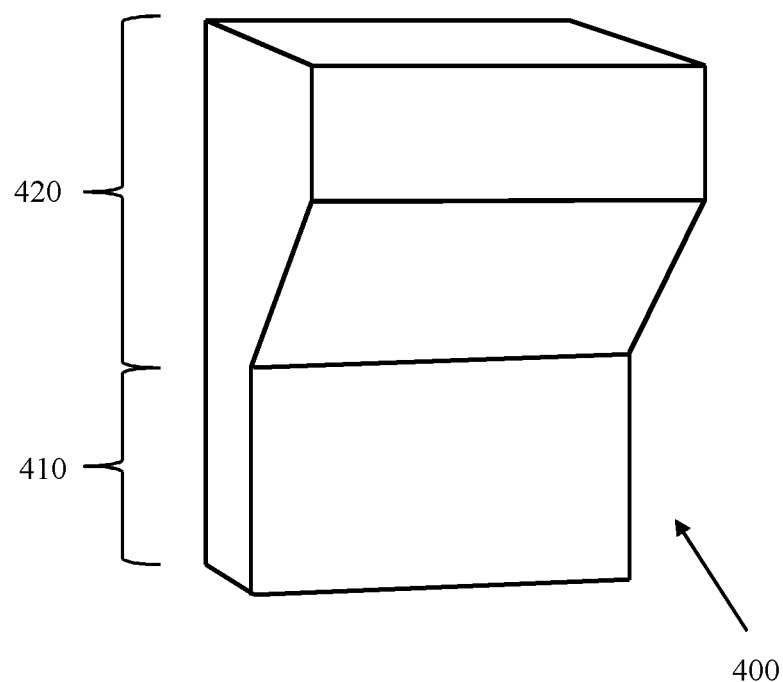
FIG. 4A shows a three dimensional representation of an X-ray modulator according to an aspect of the invention.

FIG. 4A shows a three dimensional representation of an X-ray modulator 400 according to an aspect of the invention.

In the example show in FIG. 4A, the X-ray modulator 400 comprises a window portion 410 and a single side portion 420.

Figure 4B:
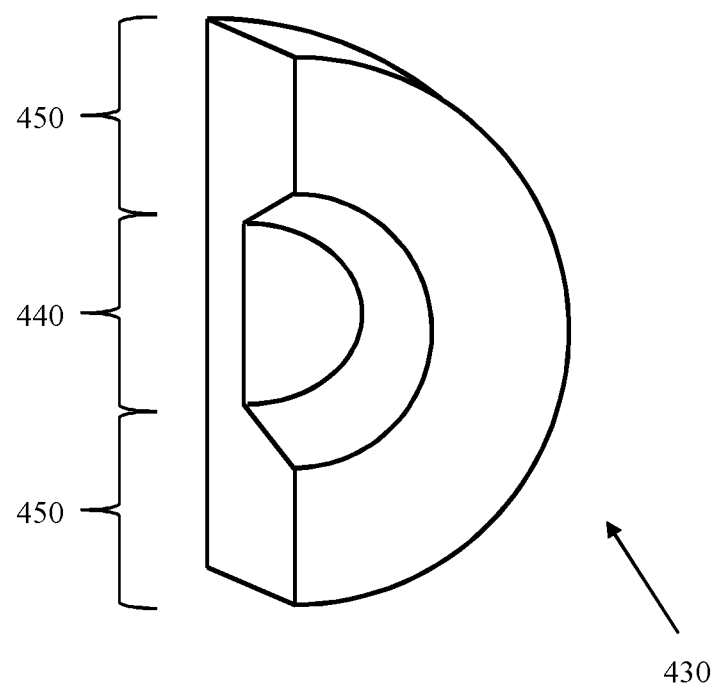
FIG. 4B shows a three dimensional representation of an X-ray modulator according to a further aspect of the invention.

FIG. 4B shows a partial three dimensional representation of an X-ray modulator 430 according to a further aspect of the invention.

In the example shown in FIG. 4B, the X-ray modulator 430 has an elliptical cross section, half of which is shown, and comprises an elliptical window portion 440 within a side portion 450 in the shape of an elliptical annulus surrounding the window portion. The ring shape of the X-ray modulator shown in FIG. 4B may help the enclosed chamber to reach the desired wave pressures. A pressure wave generated in the side portion of the ring-shaped X-ray modulator and travelling towards the window portion will be concentrated as it approaches the center of the ring, thereby increasing amplitude of the pressure wave. This is particularly the case for an X-ray modulator with a plurality of pressure modulation devices positioned about the outer ring in the side portion of the modulator.

Variations to the disclosed embodiments can be understood and effected by those skilled in the art in practicing the claimed invention, from a study of the drawings, the disclosure and the appended claims. In the claims, the word "comprising" does not exclude other elements or steps, and the indefinite article "a" or "an" does not exclude a plurality.

The mere fact that certain measures are recited in mutually different dependent claims does not indicate that a combination of these measures cannot be used to advantage.

If the term "adapted to" is used in the claims or description, it is noted the term "adapted to" is intended to be equivalent to the term "configured to".

Any reference signs in the claims should not be construed as limiting the scope.

The invention claimed is:

1. An X-ray modulator, for use with an X-ray tube, the X-ray modulator comprising:
    an enclosed chamber having a window portion and a side portion, wherein the window portion is in gaseous communication with the side portion, the enclosed chamber comprising a chamber wall, wherein the chamber wall of the window portion is thinner than the chamber wall of the side portion;

a pressure modulator provided in the side portion of the enclosed chamber and configured to modulate the pressure within the enclosed chamber; and an absorption gas within the enclosed chamber for absorbing X-ray radiation.

2. The X-ray modulator as claimed in claim 1, wherein the absorption gas comprises at least one of:

xenon; and iodine vapor.

3. The X-ray modulator as claimed in claim 1, further comprising a heating element.

4. The X-ray modulator as claimed in claim 1, wherein the absorption gas is iodine vapor, and further comprising a layer of protective material within the enclosed chamber disposed on the chamber wall.

5. The X-ray modulator as claimed in claim 1, wherein the chamber walls on opposing sides of the enclosed chamber are separated by a separation distance, wherein the separation distance at the window portion is less than the separation distance at the side portion, the side portion having a tapered structure with a minimum separation distance adjacent the window portion, the minimum separation distance being greater than or equal to the separation distance at the window portion, and a maximum separation distance distal to the window portion.

6. The X-ray modulator as claimed in claim 1, wherein the pressure modulator comprises at least one of:

a speaker;

a transducer; and an electroactive polymer.

7. The X-ray modulator as claimed in claim 1, wherein the pressure modulator is configured to modulate the pressure within an average pressure range of about 1 MPa to 35 Mpa, the average pressure being the average pressure within the enclosed chamber.

8. The X-ray modulator as claimed in claim 1, wherein the chamber wall comprises:

a first material at the side portion, the first material comprising at least one of:

aluminum;

titanium; and steel;

a second material at the window portion, the second material comprising at least one of:

beryllium;

boron carbide;

boron nitride magnesium;

diamond; and aluminum.

9. The X-ray modulator as claimed in claim 1, further comprising a pump configured to generate a flow of absorption gas between the side portion and the window portion.

10. The X-ray modulator as claimed in claim 1, further comprising a mechanical resonator.

11. The X-ray modulator as claimed in claim 1, further comprising a plurality of side portions, each side portion having a pressure modulator.

12. The X-ray modulator as claimed in claim 1, further comprising an elliptical cross section, the cross section of the side portion being an elliptical annulus and the cross section of the window portion being an ellipse within the elliptical annulus of the side portion.

13. The X-ray modulator as claimed in claim 1, wherein the X-ray modulator is disposed within a vacuum chamber.

14. A computed tomography (CT) imaging system, comprising:

an X-ray tube configured to generate X-ray radiation, the X-ray tube having an emission window for the X-ray radiation to pass through;

an X-ray modulator comprising:

enclosed chamber having a window portion and a side portion, wherein the window portion is in gaseous communication with the side portion, the enclosed chamber comprising a chamber wall, wherein the chamber wall of the window portion is thinner than the chamber wall of the side portion;

a pressure modulator provided in the side portion of the enclosed chamber and configured to modulate the pressure within the enclosed chamber; and an absorption gas within the enclosed chamber for absorbing X-ray radiation, wherein the window portion of the X-ray modulator is positioned adjacent the emission window of the X-ray tube such that the X-ray radiation generated by the X-ray tube passes through the window portion of the X-ray modulator;

a detector configured to detect X-ray radiation; and a processor configured to control the CT imaging system.

15. The CT imaging system as claimed in claim 14, wherein the system is configured to operate the X-ray tube at a first electrical tension and a second electrical tension, the first electrical tension being higher than the second electrical tension, wherein the pressure modulator is configured to modulate the pressure within the enclosed chamber between a first pressure and a second pressure, the first pressure being higher than the second pressure, and wherein the X-ray tube and the pressure modulator are operated such that the first pressure occurs at the same time as the first electrical tension and the second pressure occurs at the same time as the second electrical tension.

\* \* \* \* \*